US00PP35913P2

(12) United States Plant Patent
Ranney et al.

(10) Patent No.: US PP35,913 P2
(45) Date of Patent: Jul. 2, 2024

(54) **x *PYRACOMELES* PLANT NAMED 'NCXP2'**

(50) Latin Name: **x *Pyracomeles vilmorinii***
Varietal Denomination: NCXP2

(71) Applicant: North Carolina State University, Raleigh, NC (US)

(72) Inventors: Thomas Green Ranney, Arden, NC (US); Andra Windorf Nus, Arden, NC (US); Irene Palmer, Arden, NC (US); Nathan P. Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/206,273

(22) Filed: Jun. 6, 2023

(51) Int. Cl.
*A01H 5/02* (2018.01)
*A01H 6/74* (2018.01)

(52) U.S. Cl.
USPC ..... Plt./226

(58) Field of Classification Search
USPC ..... Plt./226
CPC ... A01H 5/02; A01H 5/08; A01H 5/00; A01H 6/74
See application file for complete search history.

(56) References Cited

PUBLICATIONS

GPN Spring Meadow Nursery Introduces New Varieties for 2023 Greenhouse Product News, retrieved on Sep. 27, 2023 at https://gpnmag.com/news/87600/, 6 pp. (Year: 2023).*
Plant Addicts Berry Box *Pyracomeles*, retrieved on Sep. 27, 2023 at https://plantaddicts.com/berry-box-pyracomeles, 4 pp. (Year: 2023).*

* cited by examiner

*Primary Examiner* — June Hwu
(74) *Attorney, Agent, or Firm* — Cassandra Bright

(57) ABSTRACT

A new and distinct cultivar of x *Pyracomeles* plant named 'NCXP2' is disclosed, characterized by abundant white flowers with showy red fruit. Plants have compact, rounded habits, and glossy green foliage. The new variety is an x *Pyracomeles*, typically produced as an outdoor ornamental plant.

3 Drawing Sheets

Latin name of the genus and species: x *Pyracomeles vilmorinii.*

Variety denomination: 'NCXP2'.

BACKGROUND OF THE INVENTION

The new cultivar is a product of a planned breeding program conducted by the inventors at a research nursery in Mills River, North Carolina. The objective of the breeding program was to produce new x*Pyracomeles* varieties with compact, rounded habits, glossy evergreen foliage, an abundance of white flowers, and showy red fruit. The open pollination resulting in the new variety was made in 2010. The seed parent is an unnamed seedling which resulted from the hybridization of the seed parent x *Pyracomeles vilmorinii* (*Pyracantha crenoserrata* x *Osteomeles subrotunda*) with the pollen parent *Pyracantha crenoserrata* (*fortuneana*) 'Cherri Berri'. This cross created a population of new hybrids, from which bulk open pollinated seed was collected. The pollen parent is unknown.

The new variety was found and selected by the inventors in 2011 at the same nursery in Mills River, North Carolina.

Asexual reproduction of the new cultivar 'NCXP2' was first performed during June of 2012 in Mills River, North Carolina, by softwood cuttings treated with a basal dip of 5,000 ppm indole butyric acid (potassium salt) in water. Through subsequent propagation, multiple additional generations have been reproduced, having shown that the unique features of this cultivar are stable and reproduced true to type.

Date of first sale was Jun. 21, 2022, in Grand Haven, Michigan. This sale was made directly by the inventor or one who obtained the claimed invention directly or indirectly from the inventor. This sale and all public sales made between Jun. 21, 2022 and the filing of this application fall within the exception allowed under 102(b)(1).

SUMMARY OF THE INVENTION

The cultivar 'NCXP2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCXP2.' These characteristics in combination distinguish 'NCXP2' as a new and distinct x *Pyracomeles* cultivar:

1. Compact, round habit.
2. Dense branching.
3. Abundant white flowers.
4. Showy red fruit.
5. Glossy evergreen foliage.

PARENT COMPARISONS

Direct parent varieties cannot be identified for comparison.

COMMERCIAL COMPARISON

Plants of the new cultivar x *Pyracomeles vilmorinii* 'NCXP2' can be compared to the commercial variety x

*Pyracomeles vilmorinii* 'NCXP1', U.S. Plant Pat. No. 31,409. Plants of 'NCXP2' are similar to plants of 'NCXP1' in most horticultural characteristics, however, plants of 'NCXP2' differ in the following:

1. Plants of the new variety have thorns, while plants of this comparator do not.
2. The new variety displays profuse amounts of white flowers followed by red fruits, while this comparator rarely produces flowers or fruit.
3. The new variety has a compact, rounded habit, while this comparator has a low, prostrate habit.

BRIEF DESCRIPTION OF THE PHOTOGRAPHS

The photographs were taken using conventional techniques and although colors may appear different from actual colors due to light reflectance it is as accurate as possible by conventional photographic techniques.

DETAILED BOTANICAL DESCRIPTION

Figure 1:
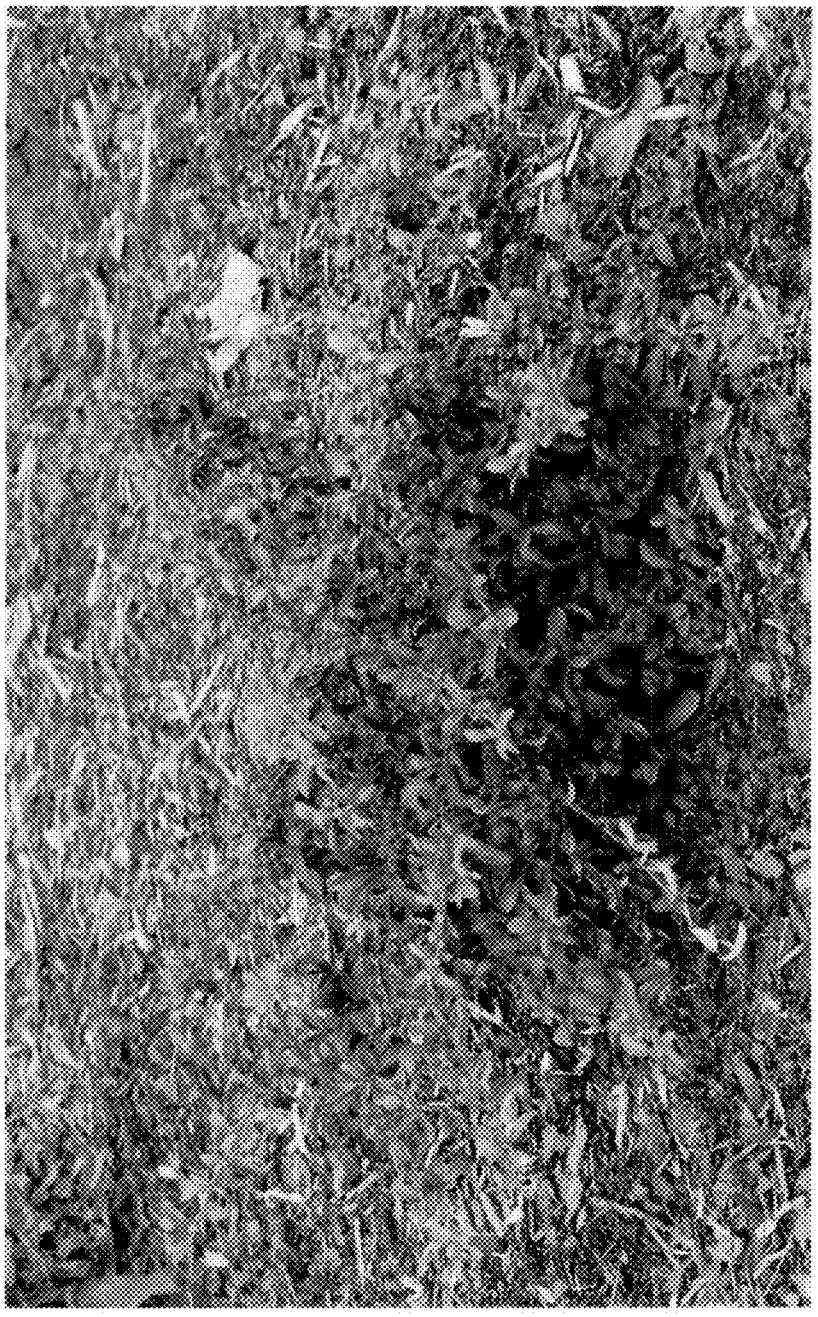
FIG. 1 is a photograph showing the compact habit of a five-year old field-grown plant in summer of 2022, in Mills River, North Carolina.
Figure 2:
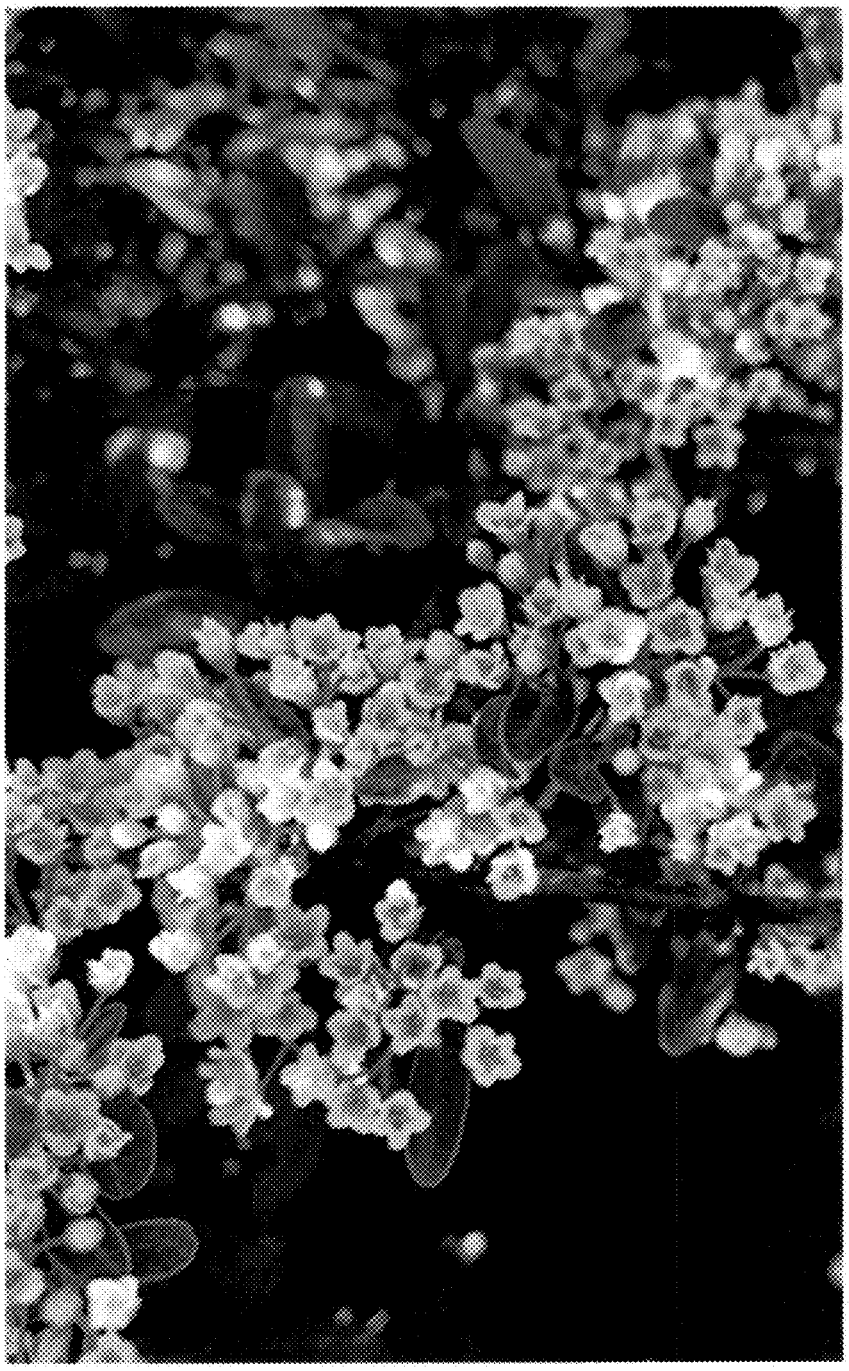
FIG. 2 is a photograph of the flowers and foliage of a five-year old field-grown plant in summer of 2022, in Mills River, North Carolina.
Figure 3:
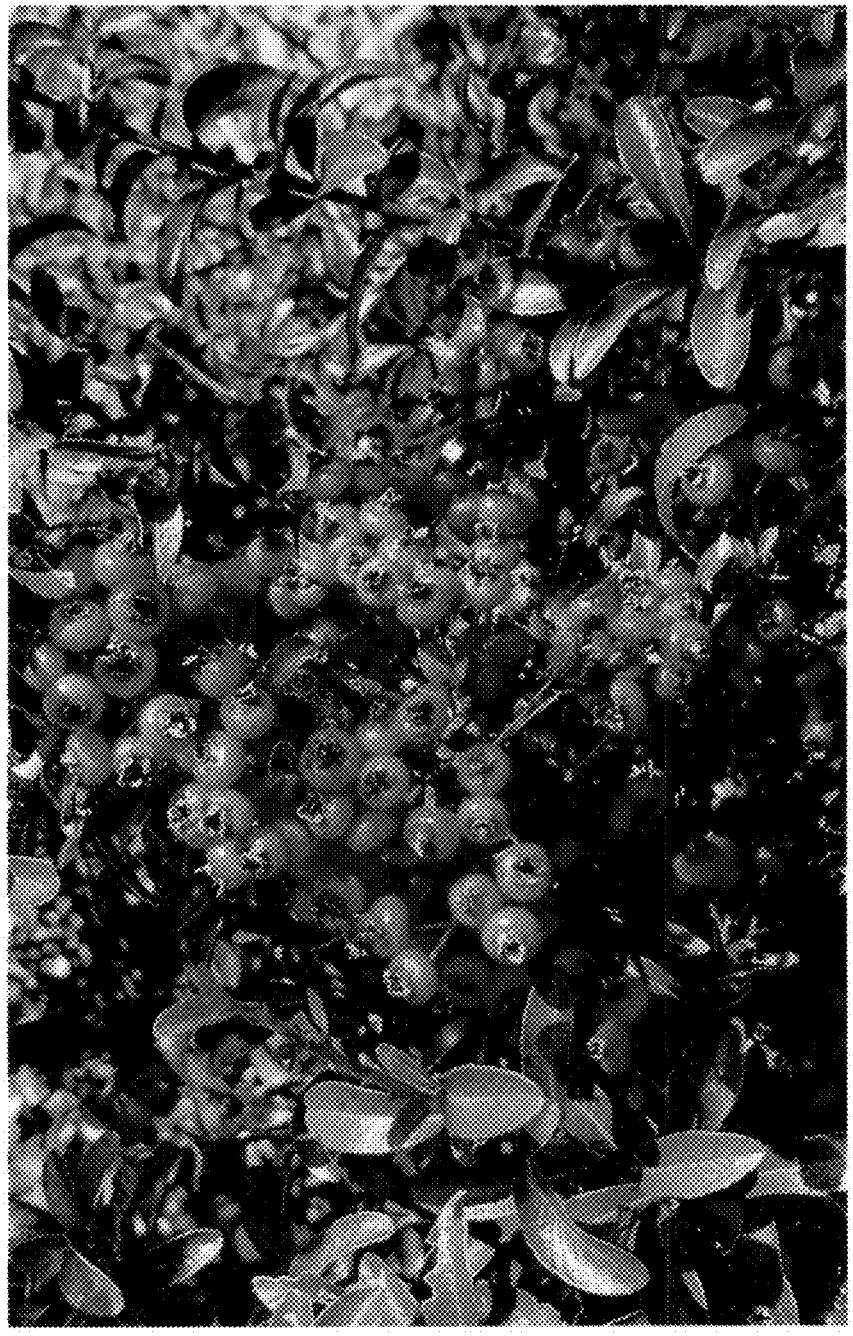
FIG. 3 is a photograph of the fruit on a five-year old field-grown plant in winter of 2022, in Mills River, North Carolina.

In the following description, color references are made to The Royal Horticultural Society Colour Chart 2015, except where general terms of ordinary dictionary significance are used. The following observations and measurements describe 'NCXP2' plants grown outdoors in Mills River, North Carolina. The plants were about 5 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: x *Pyracomeles vilmorinii* 'NCXP2'.

PROPAGATION

Typical method: Softwood cuttings.

Root initiation: 3 to 5 days in the summer at 70° F.

Time to produce rooted cutting: 6 weeks in the summer at 70° F.

Roots: Moderately dense, moderately branching, thin to medium, fibrous and fleshy. Light tan to brown in color, not accurately measured with RHS chart.

PLANT

Growth habit: Rounded and with dense branching.

Height: 100 to 150 cm.

Plant spread: 100 to 175 cm.

Age of plant described: Approximately 5 years.

Shoots:

*Current year's growth.*—

*Length.*—Average range 10 to 25 cm.

*Diameter.*—Average range 3 to 5 cm at base.

*Color.*—Upper Side: RHS Grey-Brown 166A. Under Side: RHS Brown 199B.

*Texture.*—Finely pubescent.

*Prior year's growth.*—

*Length.*—Average range 10 to 25 cm.

*Diameter.*—Average range 4 to 6 cm at base.

*Color.*—RHS Brown N200B.

*Texture.*—Glabrous.

Branches:

*Woody branches* 2-4 *years old.*—

*Length.*—Average 16.5 cm.

*Diameter.*—Average 0.7 cm.

*Color.*—RHS Brown N200B.

*Texture.*—Glabrous with lenticels of RHS Brown N200A.

Thorns:

*Length.*—Average 0.6 cm.

*Width.*—About 0.1 cm.

*Color.*—RHS Grey-Brown 166A.

*Texture.*—Glabrous.

*Density.*—0 to 4 per 10 cm of linear branch. Mainly occurring at nodes.

Internode length: Average 1.1 cm.

FOLIAGE

Leaf:

*Type.*—Simple.

*Arrangement.*—Alternate.

*Persistence.*—Evergreen.

*Shape.*—Elliptic, oblong.

*Length.*—Average 2 cm.

*Width.*—Average 0.8 cm.

*Apex.*—Variable: rounded to broadly acute.

*Base.*—Cuneate.

*Margin.*—Entire to crenulate.

*Texture.*—Mature, Upper Side: Glabrous, glossy. Mature, Under Side: Glabrous.

*Color.*—Emerging, Upper Side: RHS Yellow-Green 143C. Emerging, Under Side: RHS Yellow-Green 146D. Mature, Upper Side: RHS Green 137A. Mature, Under Side: RHS Green 138B.

*Venation.*—Type: Reticulate. Color: Upper side: RHS Green 137D. Under side: RHS Green 138C.

Petiole:

*Shape.*—Rounded.

*Length.*—Average 0.2 cm.

*Diameter.*—About 0.1 cm.

*Color.*—RHS Green 138C.

*Texture.*—Glabrous.

INFLORESCENCE

Natural flowering season: Mid-May to June in Mills River, North Carolina.

Inflorescence type: Multi-flowered corymb, held above and along the branches.

Quantity of flowers per inflorescence: About 18 (5 to 24 flowers).

Inflorescence length: Average 2.2 cm.

Inflorescence diameter: Average 2.8 cm.

Fragrance: None.

Bud:

*Length.*—About 0.2 cm.

*Diameter.*—About 0.15 cm.

*Shape.*—Oval.

*Color.*—RHS White 155C.

*Texture.*—Glabrous.

Flower:
*Shape.*—Star-shaped.
*Diameter.*—About 0.7 cm.
*Height.*—About 0.4 cm.
Petal:
*Arrangement.*—Whorled.
*Quantity.*—5 per flower.
*Shape.*—Ovate.
*Length.*—About 0.3 cm.
*Width.*—About 0.2 cm.
*Apex.*—Rounded.
*Base.*—Truncate.
*Margin.*—Entire.
*Texture.*—Glabrous.
*Color.*—RHS White NN155D.
Sepal:
*Arrangement.*—Whorled.
*Quantity.*—5.
*Shape.*—Ovate.
*Length.*—About 0.3 cm.
*Width.*—About 0.1 cm.
*Apex.*—Rounded.
*Base.*—Fused.
*Margin.*—Fused.
*Texture.*—Glabrous.
*Color.*—RHS Yellow-Green 145A.
Peduncle:
*Length.*—Average 1.8 cm.
*Diameter.*—Less than 0.1 cm.
*Texture.*—Pubescent.
*Color.*—RHS Yellow-Green 145A.
Pedicel:
*Length.*—Average 0.4 cm.
*Diameter.*—Less than 0.1 cm.
*Texture.*—Pubescent.
*Color.*—RHS Yellow-Green 145A.

REPRODUCTIVE ORGANS

Gynoecium:
*Pistil number.*—5.
*Pistil length.*—About 0.2 cm.
*Stigma color.*—RHS Yellow-Green 145C.
*Style length.*—About 0.2 cm.
*Style color.*—RHS Yellow-Green 145C.
Androecium:
*Stamen number.*—8 to 10.
*Anther shape.*—Rounded.
*Anther size.*—Less than 0.1 cm.
*Anther color.*—RHS Yellow-Green 145C.
*Pollen color.*—RHS Yellow-Green 145C.
*Pollen amount.*—Average.
Fruit:
*Type.*—Small pome with persistent calyx.
*Shape.*—Globose.
*Height.*—About 0.4 cm.
*Diameter.*—About 0.6 cm.
*Color.*—RHS Red-Orange 42A.
*Texture.*—Glabrous.
Seed:
*Quantity.*—6 to 9 per fruit.
*Length.*—About 0.2 cm.
*Width.*—About 0.1 cm.
*Color.*—RHS Black 203A.
*Texture.*—Glabrous.

OTHER CHARACTERISTICS

Disease resistance: Neither resistance nor susceptibility to the normal diseases and pests of x *Pyracomeles* has been observed.
Drought tolerance and cold tolerance: At least USDA zone 6b; testing has not been completed in colder zones.

What is claimed is:

1. A new and distinct cultivar of x *Pyracomeles* plant named 'NCXP2' as herein illustrated and described.

* * * * *